United States Patent [19] [11] 4,101,539
Kindraka et al. [45] Jul. 18, 1978

[54] BACITRACIN RECOVERY PROCESS

[75] Inventors: James Alexander Kindraka, Terre Haute, Ind.; John Bernard Gallagher, Paris, Ill.

[73] Assignee: IMC Chemical Group, Inc., Terre Haute, Ind.

[21] Appl. No.: 844,092

[22] Filed: Oct. 17, 1977

[51] Int. Cl.$^2$ ............................................. C07C 103/52
[52] U.S. Cl. .................................. 260/112.5 R; 195/96
[58] Field of Search .................... 260/112.5 R; 195/96

[56] References Cited

U.S. PATENT DOCUMENTS

| | | | |
|---|---|---|---|
| 2,774,712 | 12/1956 | Baron | 260/112.5 R |
| 2,776,240 | 1/1957 | Shortridge | 260/112.5 R |
| 3,795,663 | 3/1974 | Miescher | 260/112.5 R |

*Primary Examiner*—Delbert R. Phillips
*Attorney, Agent, or Firm*—Robert H. Dewey; Howard E. Post

[57] ABSTRACT

A process for the recovery of bacitracin from a fermented beer containing it comprising the steps of:
  a. screening the fermented beer through a 100–150 mesh screen,
  b. adjusting the pH of the fermented beer to about 7.5 to about 8.7,
  c. ultrafiltering the fermented beer in an ultrafilter having a molecular weight cut off of from 30,000 to 80,000, and
  d. collecting and holding the bacitracin containing permeate at a temperature of less than 30° C.

10 Claims, No Drawings

BACITRACIN RECOVERY PROCESS

BACKGROUND OF THE INVENTION

This invention relates to the recovery of bacitracin. In a particular aspect, this invention relates to a process for the recovery of bacitracin from a fermented beer containing it.

Bacitracin is a valuable antibiotic for topical use in the practice of medicine or as a growth promoter in animal feed supplements. The zinc salt of bacitracin is especially valuable in these uses because it is exceptionally stable over long periods of time.

The antibiotic bacitracin is produced by cultivating strains of bacteria of the *Bacillus subtilis* or *Bacillus licheniformis* groups in a suitable liquid nutrient fermentation medium. The bacitracin in the fermentation medium is present in dissolved form only in small quantities, i.e. on the order of about 300–600 units per milliliter. The separation and recovery of this small amount of material from a large volume of medium having complex character presents numerous difficulties.

Generally, a bacitracin containing solution is recovered from the fermented beer by the use of vacuum rotary drum filtration. In this procedure a filter aid such as diatomaceous earth is added to the fermented beer. The pH is then adjusted with strong acid into the range of about 3.0–3.5. The resulting material is filtered over a rotary drum filter precoated with an appropriate thickness of the same filter aid. The filtrate recovered is pH adjusted to neutrality and filtered again through a filter such as a plate and frame press to remove further impurities and filter aid particles. This filtrate is then passed to the solvent extraction step. This method can account for an 18–33% loss of the initial bacitracin. Bacitracin is lost in the pH adjusting steps due to the shock of the sudden pH shifts and is also lost in the waste filter aid. This procedure produces a cloudy filtrate to be extracted. The used filter aid also poses a solid waste disposal problem.

In the past, various procedures have been employed for recovering bacitracin from solutions containing bacitracin. One such procedure involves filtering the fermentation medium to remove solid materials, extracting the resulting filtrate containing the bacitracin with a suitable solvent for bacitracin, for example, a lower aliphatic alcohol, to form a solution of bacitracin in the alcohol, adding water to the solution, and adjusting the pH of the solution downward to less than 4.0 by addition of an acid to form a solution of bacitracin in the water. The bacitracin is then recovered from the water by suitable means, such as spray drying or freeze drying. For example, it is known from Senkus et al., U.S. Pat. No. 2,609,324 to recover bacitracin from a filtered, fermented beer containing it by extracting with butanol, extracting the bacitracin from butanol with an aqueous solution of phosphoric acid at pH 2.0, followed by a second extraction with butanol to free the bacitracin from phosphoric acid. Water was added and the butanol was then evaporated, leaving the bacitracin in aqueous solution from which it could be easily recovered by freeze drying. This process was subsequently modified to adjust the pH by treatment of the aqueous acid extract to eliminate impurities and improve the color, and the second butanol extract was also subjected to treatment designed to improve the yield. After evaporating the butanol, the bacitracin was precipitated from the aqueous solution by mixing with a solution of a zinc salt as disclosed by Zinn et al., U.S. Pat. No. 2,834,711. The precipitate was then separated and dried. Alternatively, it is known to recover the bacitracin by dehydrating the aqueous bacitracin solution by the process known as freeze drying.

Another procedure for separating bacitracin from a fermentation beer containing it is to filter the fermentation beer to remove large impurities then to sorb the bacitracin from the filtrate on a carboxylic acid type ion exchange resin. The bacitracin is eluted from the exchange resin with a weak base and recovered from the eluate by evaporation. Such a method is taught by Hodge et al. in U.S. Pat. No. 3,891,615 which employs such an ion exchange resin.

Previously employed procedures for the recovery of bacitracin including the procedures described above possess many disadvantages. The principal disadvantage is the loss of a substantial portion of the bacitracin during recovery. The primary effort of designing improvements for the recovery of bacitracin has been to develop improvements in the extraction process. Such as shown by Miescher, U.S. Pat. No. 3,795,663. There has been a long-existent need for an improved process that would further increase the recovery of bacitracin from a fermented beer over the known methods of recovery.

The prior art of which Applicants are aware is recited above in the specification and includes the following U.S. Pats.: Senkus et al., U.S. Pat. No. 2,609,324; Zinn et al., U.S. Pat. No. 2,834,711; Hodge et al., U.S. Pat. No. 3,891,615; and Miescher, U.S. Pat. No. 3,795,663. These references do not anticipate nor make obvious the process hereinafter disclosed. The reference of Senkus teaches a method of recovery of bacitracin by the extraction of the fermentor beer with butanol. The reference of Zinn discloses a method of recovery by precipitating the bacitracin from an aqueous solution by the addition of a zinc salt. The reference of Hodge discloses a method of recovery of bacitracin as the calcium or magnesium complex of an alkylbenzenesulfonic acid. All of these references describe methods of recovering the bacitracin. The references do not disclose, as does the invention described herein, how to increase the amount of bacitracin in solution from which it is to be recovered. The invention herein disclosed is for a process that precedes the recovery steps described in the above-named references. The methods of recovery described in the above references can be used in combination with the process of this invention.

SUMMARY OF THE INVENTION

It is an object of this invention to provide a process for the recovery of bacitracin.

It is another object of this invention to provide a process for the recovery of bacitracin from a fermented beer containing it.

Other objects of this invention will be apparent to those skilled in the art from the disclosure herein.

There has been found a process for the recovery of bacitracin from a fermented beer containing it comprising the steps of:

a. screening the fermented beer through a 100–150 mesh screen, b. adjusting the pH of the fermented beer to about 7.5 to about 8.7, c. ultrafiltering the fermented beer in an ultrafilter having a molecular weight cut off of from 30,000 to 80,000, and d. collecting and holding the bacitracin containing permeate at a temperature of less than 30° C.

DETAILED DESCRIPTION

The process of this invention provides an increased recovery of bacitracin from the fermented beer containing it. Bacitracin is produced in an apropriate fermentation medium by the propagation of a bacitracin producing organism such as *Bacillus subtilis* or *Bacillus licheniformis*. The process of the present invention can be used in combination with the previously known processes of extraction of bacitracin. The process of this invention is a treatment of the fermentation beer. The beer treated by the steps of this invention can then be used in the previous processes for separating bacitracin from a filtered fermentation beer by substituting the treated beer from the process of this invention for the filtered fermented beer of the known processes. The process of this invention provides a higher amount of recoverable bacitracin product per unit volume of beer for extraction by the known processes for the extraction of bacitracin.

The fermentation beer consists of a medium which will accommodate the bacitracin producing bacteria. The pH of the fermentation beer is preferably adjusted to 7.5 to 8.7. More preferably, the pH of the fermentation beer is adjusted to 7.8 to 8.1. Once the pH of the fermentation beer has been adjusted to the preferred range, the beer is screened through a 100–150 mesh screen to remove large impurities. Preferably, a 100 mesh screen is used. Screens with a mesh greater than 150 tend to be slow and clog. Screens with a mesh less than 100 may be used but will allow the passage of particles that will slow down the ultrafiltration step.

The screened beer is passed to and through ultrafiltration cartridges. The ultrafiltration cartridges can be of any size. Each ultrafiltration cartridge is filled with polysulfone resin hollow fibers. The diameter of the hollow core of each polysulfone resin fiber is from between 0.030 and 0.060 inches. A hollow core of about 0.045 inches in diameter is preferred. The active filtration surface is from 0.05 to 0.15 microns thick. It is preferred that the filtration surface be about 0.1 microns in thickness. The polysulfone resin fibers have a pore size in the range of 20 to 50 angstroms and it has been found advantageous for the pore size to be about 30 angstroms. The pore size is variable and the ultrafiltration cartridges are generally classified as to nominal molecular weight cut off, an ultrafilter with a nominal cut off in the range of 30,000 to 80,000 molecular weight is selected. Preferably, an ultrafilter with a nominal cut off of 50,000 molecular weight is utilized to filter the bacitracin fermentor beer. Ultrafilters with molecular weight cut offs greater than 80,000 do not increase significantly the amount of bacitracin recovered and those with molecular weight cut offs less than 30,000 tend to be too slow in filtering a unit volume of fermentor beer and, therefore, poorly suited for use.

The bacitracin fermentor beer is pumped through the polysulfone ultrafilters under a pressure of 20 to 35 psig. A pressure of about 25 psig is preferred. A significant backpressure of 5 to 14 psig and, preferably about 10 psig, is held on the ultrafiltration cartridges. The resulting clear permeate is in-line pHed to neutrality and collected in a holding tank under cooling conditions at a temperature of less than 30° C. The unfiltered material is recycled and combined with the screened material and is again fed through the ultrafiltration cartridges.

The bacitracin fermentor beer is a fermentation product containing the antibiotic bacitracin. The fermentation beer generally contains the raw materials of soybean flour, sugar and mineral salts; following the period of fermentation the beer becomes dark, viscous and highly proteinaceous with a pH of around 8. The fermented beer contains both the antibiotic and numerous bacterial cells of the producing organism. This whole fermentor beer, following screening, is filtered through the polysulfone ultrafilters until a volume of permeate is collected that is 50% of the initial whole fermentor beer volume. The permeate will have 33 to 36% of the whole beer's available activity of bacitracin with the remainder in the concentrated beer. The recoverable bacitracin in the permeate represents a 20 to 30% increase over the recoverable bacitracin produced by the use of rotary drum filtration.

Additional bacitracin can be recovered from the unfiltered beer. Once the whole beer has been concentrated to 50% of its original volume, a volume of water equal to the volume of permeate is added to the whole beer. The ultrafiltration again proceeds until additional permeate is collected that is equal to 50% of the diluted whole beer volume. The resultant permeate combined from the initial and diluted whole beer ultrafiltration runs contains 55 to 58% of the initial whole beer's available activity. This represents a 40 to 50% increase in activity in the permeate when rotary drum filtration is used.

Whole fermentor bacitracin beer is filtered successfully and with ease when the process of this invention using ultrafiltration is followed. Filtration rates to reach 50% concentration of the whole beer can range from 35 to 55 gallons per day per square foot of filter area.

The invention will be better understood with reference to the following examples. It is understood that these examples are intended for illustration only and it is not intended that the invention be limited thereby.

EXAMPLE 1

Five liters of bacitracin containing whole fermentor beer were screened in a 100 mesh screen. The pH of the screened beer was adjusted to a pH of 7.8 and filtered through a polysulfone resin ultrafilter at a temperature of 33° C, a pressure of 25 psig and a backpressure of 10 psig. The polysulfone ultrafilter was a cartridge 1 × 26 inches. The hollow core of each polysulfone resin fiber was 0.045 inches in diameter. The active filtration surface was 0.1 microns thick. The polysulfone ultrafilter cartridge contained 1.1 square feet of filtration surface area and had a nominal cut off of 50,000 molecular weight.

The fermentor beer was ultrafiltered until there had been collected 2400 ml of permeate. The permeate was assayed for bacitracin content. The whole beer prior to ultrafiltration had an assay of 289 units per milliliter (u/ml). The permeate had an assay of 243 u/ml and the concentrate had an assay of 310 u/ml. There was a 40% recovery of the total bacitracin from the whole fermentor beer.

The crystal clear permeate liquid was shown to have a 20–30% greater antibiotic activity than production material produced through the rotary drum filtration method. The rotary drum filtration method produced a product with an activity of from 160 to 230 u/ml.

EXAMPLE 2

The experiment of Example 1 was conducted in all essential details except the pH of the screened beer was adjusted to a pH of 7.6 and was ultrafiltered at a temperature of 30° C, a pressure of 25 psig and backpressure of 15 psig.

The 2400 ml of clear permeate obtained has an assay of 239 units of bacitracin per milliliter. This represented 33% recovery of the total bacitracin from the whole fermentor beer.

EXAMPLE 3

The experiment of Example 1 was followed in every essential detail except 10 liters of bacitracin fermentor beer were ultrafiltered at a pH of 7.7, temperature of 34° C, pressure of 25 psig and backpressure of 9 psig. Following the filtration and collection of the first 3215 ml of permeate, the ultrafilter was backflushed for 75 seconds with 325 ml of distilled water. Ultrafiltration was continued with distilled water backflushes of: 950 ml for 3 minutes following the collection of 1600 ml of permeate; 850 ml for 3 minutes following the collection of 2000 ml of permeate; 625 ml for 2½ minutes following the collection of 1400 ml of permeate; then the collection of 800 ml of permeate.

The collected fractions of permeate contained respectively: 243, 268, 245, 220, 201 and 174 units of bacitracin per milliliter or 63% of the total bacitracin from the whole fermentor beer. The initial whole beer had an assay of 329 u/ml.

EXAMPLE 4

The experiment of Example 1 was repeated in every essential detail except 6 liters of whole bacitracin fermentor beer were ultrafiltered at a pH of 7.7, 33.5° C, 25 psig and 10 psig backpressure.

A first fraction of 2000 ml permeate was collected. The ultrafiltration was then continued. Following the ultrafiltration and collection of a second fraction of 3650 ml of permeate, the ultrafilter was backflushed with a backwash of 1 liter of a buffer solution at pH 8.1 for four minutes. The ultrafiltration was then continued until another 2000 ml of permeate had been collected.

The three fractions of permeate assayed 155, 208 and 132 u/ml respectively. The combined fractions contained 56% of the bacitracin in the initial whole beer.

EXAMPLE 5

The experiment of Example 1 was repeated in every essential detail except 6 liters of whole bacitracin fermentor beer were ultrafiltered at a pH of 8.3, 39° C, 25 psig and 10 psig backpressure.

A first fraction of 2000 ml permeate was collected following the ultrafiltration of the whole beer. Next, 1380 ml of permeate were collected as the second fraction. The ultrafilter cartridge was then backflushed for 4 minutes with 500 ml of a buffer solution of pH 3.0. The ultrafiltration was continued but 500 ml of distilled water was added to the whole beer. A permeate fraction was collected consisting of 1400 ml. Again, 500 ml of distilled water was added to the whole beer and ultrafiltration continued. Following the ultrafiltration and collection of 600 ml of permeate another 500 ml of distilled water was added to the whole beer and the ultrafiltration was continued until another 50 ml of permeate had been collected.

The four permeate fractions contained respectively 255, 271, 172 and 148 u/ml or 66% of the bacitracin in the initial whole beer.

EXAMPLE 6

The experiment of Example 1 was repeated in every essential detail except 14 liters of bacitracin fermentor beer were ultrafiltered at a pH of 8.0, 36° C, 25 psig and 10 psig backpressure. A backflush buffer solution was made of 0.2% NaOH in distilled water.

The bacitracin fermentor beer was passed through the ultrafilter until 1390 ml of clear permeate were recovered which assayed 269 u/ml. Then 1270 ml of permeate were collected which assayed 302 u/ml. Then 1320 ml of permeate were collected with an assay of 318 u/ml. Then 1440 ml of permeate were collected which assayed 274 u/ml. The ultrafilter cartridge was backflushed for 90 seconds with 3000 ml of the buffer solution. Following the backflush, 400 ml of distilled water was added to the concentrated beer. Ultrafiltration was commenced and 1200 ml of permeate was collected which assayed 166 u/ml. Then 2000 ml of permeate were collected through the ultrafilter which assayed 170 u/ml. Finally, 1450 ml of permeate were collected with an assay of 180 u/ml. The total of the permeate fractions accounted for 59% of the bacitracin of the initial fermentor beer.

We claim:

1. A process for the recovery of bacitracin from a fermented beer containing it comprising the steps of:
    a. screening the fermented beer through a 100–150 mesh screen,
    b. adjusting the pH of the fermented beer to about 7.5 to about 8.7,
    c. ultrafiltering the fermented beer in an ultrafilter having a molecular weight cut off of from 30,000 to 80,000, and
    d. collecting and holding the bacitracin containing permeate at a temperature of less than 30° C.
2. The process of claim 1 in which the ultrafilter is comprised of polysulfone resin hollow fibers.
3. The process of claim 1 in which the ultrafilter has a molecular weight cut off of 50,000.
4. The process of claim 1 in which the pH of the fermented beer is adjusted to the range of 7.8 to 8.1.
5. The process of claim 1 in which the fermented beer is passed through the ultrafilter at a pressure of from 20 to 35 psig and backpressure of from 5 to 14 psig.
6. The process of claim 5 in which the pressure is 25 psig and backpressure is 10 psig.
7. The process of claim 1 in which the ultrafiltering step is conducted until ¼ to ½ of the total volume of fermentation beer has been collected as permeate, backflushing the ultrafilter with a backflush solution, continuing the ultrafiltration of the combined fermentor beer and backflushed material.
8. The process of claim 7 in which the backflush solution is water.
9. The process of claim 7 in which the backflush solution has a pH from about 3 to about 7.
10. The process of claim 7 in which the backflush solution has a pH from about 7 to about 9.

UNITED STATES PATENT AND TRADEMARK OFFICE
CERTIFICATE OF CORRECTION

PATENT NO. : 4,101,539
DATED : July 18, 1978
INVENTOR(S) : James A. Kindraka et al It is certified that error appears in the above-identified patent and that said Letters Patent are hereby corrected as shown below:

Column 3, line 7, "apropriate" should read -- appropriate --

Column 6, line 1, "50 ml" should read -- 500 ml --

Signed and Sealed this

Fifteenth Day of May 1979

[SEAL]

Attest:

RUTH C. MASON
Attesting Officer

DONALD W. BANNER
Commissioner of Patents and Trademarks